United States Patent
Lin et al.

(10) Patent No.: US 6,992,127 B2
(45) Date of Patent: Jan. 31, 2006

(54) POLYMERIC COATINGS CONTAINING A PH BUFFER AGENT

(75) Inventors: Tung-Liang Lin, Acton, MA (US); Min-Shyan Sheu, Chelmsford, MA (US); Ih-Huong Loh, Lexington, MA (US)

(73) Assignee: AST Products, Inc., Billerica, MA (US)

( * ) Notice: Subject to any disclaimer, the term of this patent is extended or adjusted under 35 U.S.C. 154(b) by 63 days.

(21) Appl. No.: 10/303,226

(22) Filed: Nov. 25, 2002

(65) Prior Publication Data

US 2004/0102558 A1 May 27, 2004

(51) Int. Cl.
C08L 3/32 (2006.01)

(52) U.S. Cl. .............. 524/414; 524/415; 524/417; 524/438; 524/589; 524/590; 424/423; 424/411; 427/2.12; 427/2.13

(58) Field of Classification Search .............. 524/590, 524/417, 438, 589; 604/21, 264; 424/423
See application file for complete search history.

(56) References Cited

U.S. PATENT DOCUMENTS

| | | | |
|---|---|---|---|
| 4,054,139 A | 10/1977 | Crossley | 128/260 |
| 4,326,532 A * | 4/1982 | Hammar | 604/266 |
| 4,527,293 A * | 7/1985 | Eckstein et al. | 623/23.68 |
| 4,642,104 A | 2/1987 | Sakamoto et al. | 604/264 |
| 4,906,466 A | 3/1990 | Edwards et al. | 424/78 |
| 5,135,516 A * | 8/1992 | Sahatjian et al. | 604/265 |
| 5,217,493 A | 6/1993 | Raad et al. | 623/11 |
| 5,403,295 A * | 4/1995 | Byrne | 604/265 |
| 5,520,664 A | 5/1996 | Bricault, Jr. et al. | 604/265 |
| 5,554,147 A | 9/1996 | Batich et al. | 604/890.1 |
| 5,603,955 A * | 2/1997 | Gehrke et al. | 424/484 |
| 5,607,417 A | 3/1997 | Batich et al. | 604/890.1 |
| 5,670,558 A * | 9/1997 | Onishi et al. | 523/112 |
| 5,672,638 A * | 9/1997 | Verhoeven et al. | 523/112 |
| 5,788,687 A | 8/1998 | Batich et al. | 604/890.1 |
| 5,820,918 A | 10/1998 | Ronan et al. | 427/2.1 |
| 5,848,995 A | 12/1998 | Walder | 604/265 |
| 5,873,904 A | 2/1999 | Ragheb et al. | 623/1 |
| 5,877,243 A | 3/1999 | Sarangapani | 524/139 |
| 5,895,713 A * | 4/1999 | Miyazaki et al. | 428/335 |
| 6,096,018 A | 8/2000 | Luzio et al. | 604/500 |
| 6,228,393 B1 | 5/2001 | DiCosmo et al. | 424/450 |
| 6,273,875 B1 | 8/2001 | Siman et al. | 604/264 |
| 6,306,422 B1 | 10/2001 | Batich et al. | 424/423 |
| 6,361,526 B1 | 3/2002 | Reisdorf et al. | 604/265 |
| 6,368,356 B1 * | 4/2002 | Zhong et al. | 623/23.75 |
| 2002/0009485 A1 * | 1/2002 | DiCosmo et al. | 424/446 |
| 2003/0031699 A1 * | 2/2003 | Van Antwerp | 424/423 |

FOREIGN PATENT DOCUMENTS

EP 882 461 A2 * 12/1998

* cited by examiner

*Primary Examiner*—David W. Wu
*Assistant Examiner*—Rip A. Lee
(74) *Attorney, Agent, or Firm*—Fish & Richardson P.C.

(57) ABSTRACT

A device containing a support member, a cross-linked polymer, and a pH buffer agent. A surface of the support member is coated with the cross-linked polymer in which the pH buffer agent is embedded.

5 Claims, No Drawings

POLYMERIC COATINGS CONTAINING A PH BUFFER AGENT

BACKGROUND

Calcium and magnesium phosphates tend to precipitate on surfaces of implant devices, a phenomenon called "encrustation." See J. Urol. (1988) 139:37–38 and Br. J. Urol. (1994) 73:687–691. It has been suggested that encrustation on surfaces of urethral stents is mainly due to (1) the high pH of urine, which promotes formation of calcium and magnesium phosphates; (2) growth of bacteria, which convert urea in urine to ammonia, thereby further increasing the pH of urine; and (3) rough and hydrophilic surfaces, which create nuclei sites for encrustation. Such encrustation frequently leads to blockage and fracture of implant devices.

SUMMARY

This invention relates to embedding a pH buffer agent in a polymeric coating on a device, e.g., a urethral stent, a heart valve, or a sample stick.

In one aspect, the invention features a kit containing a pH buffer agent, a cross-linkable polymer, and a cross-linking compound for cross-linking the polymer. This kit can be conveniently used to coat implant devices to protect them from encrustation, or to coat a sample stick to prevent or minimize undesirable pH change. More specifically, the pH buffer agent can include a proper amount of mixture of inorganic salts, such as potassium phosphate monobasic and sodium phosphate. When dissolved in an aqueous solution, the buffer agent maintains a predetermined pH (e.g., 6.4) or pH range (e.g., 6–6.8). Preferably, the polymer, either hydrophobic or hydrophilic, is water-based; namely, it can be dissolved or dispersed in water. The kit can be used to prepare a coating solution by dissolving or dispersing the pH buffer agent, the polymer and the cross-linking compound in an aqueous solvent. The coating solution is then applied to a surface of a device to form a coating.

In another aspect, the invention features a coated device that can be prepared using the method described above or by other methods. The device includes a support member (e.g., an uncoated urethral stent), a cross-linked polymer, and a pH buffer agent. In this device, a surface of the support member is coated with the cross-linked polymer in which the pH buffer agent is embedded. The pH of the coated surface can be substantially maintained even when the device is exposed to an environment of undesirable pH.

The details of one or more embodiments of the invention are set forth in the accompanying description below. Other features, objects, and advantages of the invention will be apparent from the detailed description, and from the claims.

DETAILED DESCRIPTION

The invention is based on an unexpected discovery that a pH buffer agent can be embedded in a polymeric coating on a surface of a device, thereby maintaining the pH of the coated surface.

Within the scope of this invention is a kit for providing a coating, in which a pH buffer agent is embedded. Such a kit contains a pH buffer agent, a cross-linkable polymer, and a cross-linking compound.

Examples of a suitable pH buffer agent include a mixture of inorganic salts (e.g., two carbonate salts or two phosphate salts) or a mixture of organic compounds (e.g., acetic acid and its conjugate base). Such an agent, when coated on the surface of a device, is capable of maintaining the surface pH within a certain range when the device is exposed to an aqueous solution of undesirable pH. One can increase the buffer capacity by increasing the amount of the buffer agent.

A cross-linkable polymer can be a homo-polymer (e.g., acrylic polymer and epoxy polymer) or a copolymer (e.g., polyurethane, polyamide, and polyester) containing one or more functional groups, such as carboxylate group, hydroxyl group, amine group, and epoxy group. One can cross-link two or more polymer molecules, in the presence of a buffer agent, by reacting the functional groups on the polymer molecules with the functional group(s) on a cross-linking compound molecule. The cross-linked polymer entraps the pH buffer agent. Examples of a suitable cross-linking compound include any organic compounds containing one functional group (such as carboiimide group), or containing two or more functional groups (such as aziridine group, epoxy group, silane group, or isocyanate group). Cross-linking compound molecules, such as those containing chlorosilane groups, can react among themselves to form a matrix to stabilize the polymer.

As an example, one can use a polyurethane having carboxylate groups as a cross-linkable polymer and a compound having two aziridine groups as a cross-linking compound. More specifically, carboxylate groups on two polyurethane molecules can, respectively, react with the two aziridine groups on a cross-linking compound molecule, resulting in formation of cross-linked polyurethane molecules. A compound containing one carboiimide group or two epoxy groups can also be used to cross-link the just-mentioned polyurethane molecules in an analogous way. In another example, poly(ethylene glycol), a hydroxyl group-containing polymer, can be cross-linked by a cross-linking compound having two isocyanate groups.

The kit can further contain a bioactive agent, e.g., a bactericide or an anti-thrombogenic agent. A bactericide, e.g., silver chloride, when present in a coating of an implant device, reduces bacterial adherence to the device. An anti-thrombogenic agent, e.g., heparin, when present in a coating of an implant device, can prevent blood from coagulation. As discussed below, a kit containing an anti-thrombogenic agent can also include a hydrophilic polymer, e.g., polyvinylpyrolidone (PVP). Alternatively, the kit can contain reagents required in a coating of a sample stick for detection of a chemical entity in a specimen.

The kit can be readily used to coat a device. A coating solution is first prepared by dissolving or dispersing the pH buffer agent, the polymer, and the cross-linking compound, as well as a bioactive agent and the like, if any, in a solvent. The solvent can be an organic solvent, an aqueous solvent or a mixture of two or more solvents, depending on the solubility of each of the solutes. The solution is then applied onto a surface of the support member (e.g., by dipping, spraying, or painting), followed by the removal of the solvent (e.g., air dried or heated in an oven) to form a coating. Cross-linking of the polymer takes place either when the solvent is present in the coating or after the solvent has been removed from the coating. When the polymer is a liquid, a coating solution may be prepared by dissolving the pH buffer agent and the cross-linking compound in the polymer without using a solvent. The polymer is cross-linked after the solution has been applied onto a surface of a support member.

The invention also features a coated device. That is, a support member coated with a cross-linked polymer in which a pH buffer agent is physically or chemically embedded. The polymer can be cross-linked by either using a cross-linking compound (e.g., a component in a kit of this invention) or using other cross-linking methods (e.g., UV cross-linking of a polymer containing epoxy groups).

In addition to being physically trapped by a cross-linked polymer, the pH buffer agent can further interact with the polymer via covalent bonding, hydrogen bonding, or ionic bonding, thereby further prolonging the coated device's resistance to pH change. Such bonding can be formed between suitable ionic groups/functional groups of the polymers and the pH buffer agent. Similarly, the pH buffer agent can also be linked, via covalent bonding, hydrogen bonding or ionic bonding, to a functionalized or ionized surface of the support member. The cross-linked polymer can also be bonded to a surface of the support member in a similar manner. Further, a hydrophilic polymer can also be included in a coating of a device of this invention, especially when an anti-thrombogenic agent, is embedded in the coating. Anti-thrombogenic agents are water-soluble. When the device is placed in the body, the presence of a hydrophilic polymer facilitates absorption of water onto the coating, dissolution of the anti-thrombogenic agent in the water, and the release of the anti-thrombogenic agent.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

1.7 g of a buffer agent, pHydrion (a powdery mixture of potassium phosphate monobasic and sodium phosphate dibasic, Micro Essential Laboratory Inc., Brooklyn, N.Y.) certified at pH 6.40 in an aqueous solution, was dissloved in 60 mL de-ionized water by stirring for 20 minutes. 200 g of water-based carboxylate-containing polyurethane (NeoRez R-9621, NeroResins Inc., Wilmington, Mass.) was then dispersed in the buffer solution by stirring for 20 minutes. Finally, 3 g of a cross-linking compound containing two or more aziridine groups (CX-100, NeroResins Inc., Wilminton, Mass.) was added to the solution, followed by stirring for 30 minutes.

White polyurethane tubes (Chronoflex, 8F×30 cm, Futuremed Interventional, Athens, Tex.) were pre-cleaned with 2-propanol and dip-coated in the above solution at a withdrawing speed of 10 inches per minute. The coated tubes were then dried in a 65° C. oven for 2.5 hours.

A 1% cresol red in alcohol was used to examine the coating. The coated surface turned from red (indicating pH between 7–8.8) to bright yellow color (indicating pH below 7), evidence that the pH buffer agent was capable of maintaining a pH below 7. The color of the un-coated surface remained the same.

EXAMPLE 2

White polyurethane (Chronoflex) tubes were coated following the same procedures described in Example 1, except that 21.75 mL of AgCl solution (8% AgCl in $NH_4OH$) was additionally included in the coating solution. Each of 20 coated polyurethane tubes (4 cm long) was placed into a vial containing 20 mL of artificial urine. The vial was kept at room temperature and the artificial urine was replaced daily. Samples were taken from each vial on the 8th, 15th, 22nd, and 30th days to determine the pH of the coating with four pH indicators, i.e., bromophenol blue, methyl red, bromothymol blue, and cresol red. The results indicate that the pH of all coatings was maintained at 5.0–6.0 throughout the experiment. Note that the pH of the pHydrion buffer agent, as a powder, was also 5.0–6.0, as determined with the same pH indicators.

EXAMPLE 3

Polyurethane (PU)-coated tubes (Chronoflex) were coated following the same procedures described in Example 1, except that 21.75 mL of AgCl solution (8% AgCl in $NH_4OH$) was additionally included in the coating solution.

PVP-coated tubes, i.e., urethral stents were obtained from Bard Urology (Atlanta, Ga.) for comparison.

Two in vitro encrustation tests, including a 5-week study (4 runs) and a 10-week study (8 runs), were performed to quantify precipitation of calcium deposits on both PU-coated tubes and PVP-coated tubes from human urine. See, BJU International (2000) 86:414–421. The amount of calcium encrustation on each tube was measured using atomic absorption spectroscopy (Unican 929 AA spectrometer, Unicam Ltd., Cambridge, England). In all 12 runs, PU-coated tubes, whose coating contained a buffer agent, always showed less calcium encrustation than PVP-coated tubes, whose coating was free of a buffer agent.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A kit for preparing a solution for coating a medical device, the kit comprising a pH buffer agent, a cross-linkable polymer, and a cross-linking compound for cross-linking the polymer, wherein the pH buffer agent, the cross-linkable polymer, and the cross-linking compound are three components of the coating solution, the pH buffer agent minimizes pH changes on the surface of the medical device; the pH buffer agent including inorganic salts, the cross-linkable polymer being polyurethane having carboxylate groups, and the cross-linking compound being an aziridine, carbodiimide, or epoxy silane.

2. The kit of claim 1, wherein the cross-linking compound is an aziridine and the pH buffer agent includes potassium phosphate monobasic and sodium phosphate dibasic so as to maintain pH 6–6.8.

3. The kit of claim 1, further comprising silver chloride as a component of the coating solution.

4. A medical device comprising a support member, a cross-linked polymer, and a pH buffer agent, wherein a surface of the support member is coated with the cross-linked polymer in which the pH buffer agent is embedded, and the pH buffer agent minimizes pH changes on the surface of the support member; the pH buffer agent including potassium phosphate monobasic and sodium phosphate dibasic so as the maintain pH 6–6.8, and the cross-linked polymer being water-based, hydrophobic polyurethane.

5. The device of claim 4, further comprising silver chloride embedded in the cross-linked polymer.

* * * * *